(12) United States Patent
Cordray

(10) Patent No.: US 7,678,389 B1
(45) Date of Patent: *Mar. 16, 2010

(54) TREATMENT OF OPTIC AND OTIC INFLAMMATION

(76) Inventor: Scott Cordray, 725 Country Woods Way, Sapulpa, OK (US) 74066

( * ) Notice: Subject to any disclaimer, the term of this patent is extended or adjusted under 35 U.S.C. 154(b) by 1351 days.

This patent is subject to a terminal disclaimer.

(21) Appl. No.: 10/869,264

(22) Filed: Jun. 16, 2004

(51) Int. Cl.
*A61K 33/14* (2006.01)
(52) U.S. Cl. .................. 424/678; 424/679; 424/681; 424/697
(58) Field of Classification Search .................. 424/678, 424/679, 681, 697
See application file for complete search history.

(56) References Cited

U.S. PATENT DOCUMENTS

| | | | | |
|---|---|---|---|---|
| 4,370,325 A | * | 1/1983 | Packman | 514/335 |
| 4,961,927 A | * | 10/1990 | Kogure | 424/94.3 |
| 6,767,874 B2 | * | 7/2004 | Gonzalez | 510/109 |
| 2004/0084383 A1 | * | 5/2004 | Zhou et al. | 210/754 |

* cited by examiner

*Primary Examiner*—Zohreh A Fay
(74) *Attorney, Agent, or Firm*—John Lezdey & Assoc

(57) ABSTRACT

There is provided a method of treating irritations and inflammation of the eye or ear by the topical administration of an aqueous composition containing magnesium, potassium and sodium halides. The eye treating compositions have an osmolarity between 140 and 180 mOsm/l and are hypotonic.

7 Claims, No Drawings

TREATMENT OF OPTIC AND OTIC INFLAMMATION

FIELD OF THE INVENTION

The present invention relates to non-steroidal anti-inflammatory compositions for treating optic and/or otic inflammations and irritations. More particularly, there is provided a composition of inorganic salts which can be used over a long period of time to reduce inflammation and remove irritants.

BACKGROUND OF THE INVENTION

Ocular irritations can result from various ophthalmic surgical procedures, contact lens wear, exposure to allergens, ocularly irritating chemical, pollutants, dust particles, ultraviolet light, including various pathogens that cause conjunctivitis.

Ear infections and irritations results from exposure to pathogens while swimming, ear wax build up, insects, and exposure to chemical vapors.

Prompt prophylaxis treatment by ear and eye washes will aid in reducing the length and severity of any irritation.

U.S. Pat. No. 5,110,493 to Cherng-Chyi et al relates to ophthalmic non-steroidal anti-inflammatory drug formulations containing a quaternary ammonium preservative and a non-ionic surfactant.

There are a number of patents that address various ophthalmic formulations to ease ocular irritations, for example, U.S. Pat. Nos. 5,895,645; 5,877,154; 5,872,086 and 5,861,148.

Since many different number of factors are involved in causing eye and ear irritations and inflammations, it would be preferable to have a method of treatment which can reduce the allergens or irritants that can be used over long periods of time as well as to treat inflammations that can be used by children as well as adults.

SUMMARY OF THE INVENTION

There is provided an aqueous composition and method for treating the symptoms associated with the irritation and inflammation of the eyes and ears caused by allergens and irritants. More particular, there is provided a method of irrigating and treating the eyes and ears with an aqueous composition comprising a) About 0.01 to 5 percent by weight of salts comprising 1) About 45 to 60% of magnesium chloride, 2) About 29 to 41% of potassium chloride, and 3) About 1 to 4% of sodium chloride.

b) The remainder being water.

Preferably, the composition is buffered by a pH of about 4.0 to 8.0, a preferred pH range is about 5.0 to 6.8.

Advantageously, the composition also contains about 0.01 to 5% by weight of salts selected from the group consisting of magnesium bromide, calcium chloride, calcium bromide, sodium bromide and magnesium sulfate (Epsom salts).

It is further advantageous to have the optic compositions hypotonic.

It is therefore an object of the invention to provide a method for the treatment of irritations and inflammations of the eyes and ears with an aqueous composition comprising magnesium and potassium chloride.

It is another object of the invention to reduce the presence of allergen and irritants in the eyes and ears by irrigation with an aqueous composition comprising inert salts.

DESCRIPTION OF THE PREFERRED EMBODIMENTS

The present invention relates to a method of treating a patient suffering from an irritation and/or inflammations of the eyes and ears. More particularly, there is provided a method of topically administering an effective amount of an aqueous composition comprising.

A) About 0.01 to 5% by weight, of salts comprising:

1) About 45 to 60% of magnesium chloride, preferably about 55 to 58%.

2) About 20 to 41% of potassium chloride, preferably about 30 to 40%, and

3) About 0 to 4% of sodium chloride, preferably about 1 to 2%, and

B) The remainder water, whereby the irritation and/or inflammation is reduced.

The composition is at a pH between 4.0 and 8.0 preferably at a pH between 5.0 and 6.8. The buffer can comprise a buffer selected from the groups comprising sodium phosphate, potassium phosphate, sodium carbonate and the like as is commonly used by those skilled in the art.

The composition can include other inorganic salts selected from the group consisting of magnesium bromide, potassium bromide, calcium chloride, magnesium sulfate, calcium bromide or a mixture thereof in amount of about 0.5 to 4%.

In one embodiment, the carrier for optic compositions is a sterile, aqueous solution that is buffered with compounds such as phosphate buffers, carbonate buffers and the like. The composition is preferably provided as a buffered aqueous solution having a viscosity of from about 1 to 50 centipoise (cps). In another embodiment, the composition is formulated as a viscous liquid having a viscosity of between about 50 and several thousand cps using viscosity-enhancing agents such as, for example propylene glycol, hydroxymethyl cellulose or glycerin.

Other ophthalmic pharmaceutical carriers are also contemplated, including, for example, gels and ointments. The formulations can also comprise ingredients which regulate the osmolarity of the final formulation, as well as the pH of the formulations.

For example, the resulting preparations for ocular use are advantageously hypotonic, and have an osmolarity of between about 140 and 280 mOsm/l, and pH of between about 6.8 and 7.6. The osmolarity of the solutions can be adjusted by means of well known osmolarity adjusting agents such as sodium chloride, potassium chloride and monosaccharides. Alternatively, the resulting preparations can be isotonic, or in another embodiment, the resulting preparations can be hypertonic. The present formulations may also contain other conventional ingredients used in ophthalmic preparations, such as dextrose, preservatives (e.g. Thimerosal™, i.e., sodium ethylmercurithiosalicylate (Sigma; /St. Louis, Mo.), benzalkonium chloride), analgesics (e.g., ibuprofen), antibiotics (e.g., gentamicin, streptomycin), antioxidants (e.g. ascorbic acid, BHA, BHT), demulcents (e.g., glycerin, propylene glycol), and the like. Descriptions of compounds used in standard ophthalmic formulations may be found in, for example, Remington's Pharmaceutical Sciences, latest edition, Mack Publishing Co. Easter, Pa., and in U.S. Pat. Nos. 5,951,971; 5,861,148 and 5,800,807.

The pH of the formulations described herein can also be adjusted to the desired value by adding an acid, such as hydrochloric acid, or a base such as sodium hydroxide, until the pH of the formulation falls within the range described above. Such adjustments are preferably made without increasing the ionic strength of the formulation to beyond acceptable levels.

The present compositions are prepared according to conventional techniques by mixing the relative ingredients in appropriate amounts in sterile water, or preparing gels and ointments using gel and ointment preparation techniques well known in the pharmaceutical arts. In preferred embodiments, the formulations are sterilized prior to use.

The formulations described herein are administered to the eyes or ears of a subject, preferably an animal such as a dog, cat, bird, reptile or amphibian, more preferably a mammal, most preferably a human, by any route and through any means where delivery of the formulation to the site of irritation can be achieved. For example, the formulations are administered by spray, by gel, by eye drop, or by other methods of administration well known to those of skill in the relevant art. In one embodiment of the present invention, daily dosages in human therapy of the present formulations are of about 1-2 drops per eye or ear, administered about 1-8 times a day (for instance by means of a standard pharmacopedial medicinal dropper of 3 mm in external diameter, which when held vertically delivers 20 drops of water of total weight of 0.9-1-1 grams of 25. degree.C.)

Other non-steroidal anti-inflammatory agents which may be included in the formulations are analgesic/nonsteroidal anti-inflammatory compounds. Preferably the non-steroidal anti-inflammatory agent is one or more of the following: aspirin, benoxaprofen, benzofenac, bucloxic acid, butibufen, carprofen, cicloprofen, cinmetacin, clidanac, clopirac, diclofenac, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketroprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac. Preferably, the agent is selected from the group consisting of diclofenac, suprofen, and flurbiprofen sodium and mixtures thereof.

The compositions may contain water soluble polymers or water insoluble polymers as suspending agents. Examples of such soluble polymers are cellulosic polymers like hydroxypropyl methylcellulose. Water insoluble polymers are preferably crosslinked carboxy-vinyl polymers. It is important to note, however, that the present invention may require one of the active ingredients to be in suspension without reference to whether the polymer is or is not in suspension.

A preferred form of the invention incorporates insoluble polymers to provide a gel or liquid drops which release the drug over time. Preferably, the polymer is about 0.1 to 6.5%, more preferably about 1.0 to about 1.3% by weight based on the total weight of the suspension of a crosslinked carboxy-containing polymer. Suitable carboxy-containing polymers for use in the present invention and method for making them are described in U.S. Pat. No. 5,192,535 to Davis et al. which is hereby incorporated by reference and relied upon. These polymer carriers include lightly crosslinked carboxy-containing polymers (such as polycarbophil, or Carbopols®), dextran, cellulose derivatives, polyethylene glycol 400 and other polymeric demulcents such as polyvinylpyrolidone, polysaccharide gels and Gelrite®. A carboxy-containing polymer system known by the tradename DuraSite®, containing polycarbophil, is a sustained release topical ophthalmic delivery system that releases the drug at a controlled rate, may also be used.

Aqueous mixtures of this invention may also contain amounts of suspended lightly crosslinked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or opthalmologically harmful constituents, and will be adjusted to a pH of from about 4.0 to 6.8, and preferably from about 5.5 to about 6.5, using any physiologically and opthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylamino-methane), or the like and salts and buffers such as citrate/dextrose, sodium bicarbonate, ammonium chloride and mixtures of the aforementioned acids and bases.

When formulating the aqueous suspensions, ophthalmic compositions, their osmotic pressure (.pi.) may be adjusted to from about 10 milliosmolar (mOsM) to about 400 mOsM, using appropriate amounts of physiologically and opthalmologically acceptable salts. Sodium chloride is preferred to approximate physiologic fluid, and amounts of sodium chloride ranging from about 0.01% to about 1% by weight, and preferably from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated ranges. Sugars like mannitol, dextrose, glucose or other polyols may be added to adjust osmolarity.

When water soluble polymers are used, such as hydroxypropyl methylcellulose, the viscosity will typically be about 10 to about 400 centipoises, more typically about 10 to about 200 centipoises or about 10 to about 25 centipoises.

Non-steroidal anti-inflammatory agents are non-steroidal substances used in treating or ameliorating a disease or medical condition. They include drugs intended to treat therapeutically conditions of the eye or ear itself or the tissue surrounding the eye or ear and drugs administered to treat therapeutically a local condition other than that involving the eye or ear. The ophthalmic medicaments will typically be incorporated in the topical delivery systems of this invention in therapeutically active amounts comparable to amounts administered in other dosage forms, usually in amounts ranging from about 0.001% to about 5% by weight, and preferably from about 0.1% to about 1% by weight, based on the total weight of the formulation. Thus, for example, about 0.1% to about 1.0% by weight of the anti-inflammatory non-steroidal compounds can be administered in this manner.

In general, ophthalmic and optic formulations suitable for topical administration may be formulated and administered in accordance with techniques familiar to persons skilled in the art. The finished formulations are preferably stored in opaque or brown containers to protect them from light exposure, and under an inert atmosphere. These aqueous suspensions can be packaged in preservative-free, single dose non-reclosable containers. This permits a single dose of the medicament to be delivered to the eye or ear as a drop or ribbon, with the container being discarded after use. Such containers eliminate the potential for preservative-related irritation and sensitization, as has been observed to occur particularly from medicaments containing mercurial preservatives. Multiple dose containers can also be used, if desired, particularly since the relatively low viscosities of the aqueous suspensions of this invention permit constant, accurate dosages to be administered drop-wise as many times each day as necessary. In those suspensions where preservatives are to be included, suitable preservatives are chlorobutanol, polyquat, benzalkonium chloride, cetyl bromide, sorbic acid and the like.

In order that those skilled in the art can more fully appreciate aspects of this invention, the following examples are set forth. These examples are given solely for purposes of illustration and should not be considered as expressing limitations.

Example 1

A preferred 100 ml composition of the present invention comprises

| Ingredient | Wt. |
|---|---|
| Magnesium Chloride | 1.0-2.00 g |
| Magnesium Bromide | 0.01-0.05 |
| Magnesium Sulfate | 0.01-0.05 |
| Potassium Chloride | 0.8-1.00 g |
| Calcium Chloride | 0-0.05 g |
| Sodium Carbonate | 0-0.05 g |
| 1% Saline Solution | q.s. |

The pharmaceutical compositions may be prepared for eye or ear administration according to standard formulating procedures.

The salts may be dissolved in sterile water, physiological saline solution or buffer solution with a pH of 5.0 to 6.8 which is advantageously ionically balanced. For example, the preferred formulation for borax buffer is as follows:

Solution A-1.9 g $Na_2P_4O_7$ per 100 ml of $H_2O$.

Solution B-1.25 g $H_3BO_3$+0.3 g NaCl per 100 ml $H_2O$ is mixed with Solution A and the salts are added.

It is preferred to include a preservative, for example, Thimerosal or benzalkonium chloride and/or an antioxidant, for example, vitamin E. Other filler materials which can be included and are commonly found in ear and eye compositions include sodium carbonate solution, sorbitol solution, particularly potassium sorbate solution with a pH of 6-6.5, polyethylene glycol and the like.

Example 2

A composition which is effective as eye drops is prepared as follows:

| Ingredient | Weight |
|---|---|
| Magnesium Chloride | 1.0 mg |
| Potassium Chloride | 1.0 mg |
| 10% Saline Solution | 97.9 |
| Anti-Oxidant | 0.1 mg |

The composition may additionally include 0.5% of magnesium sulfate and 0.5% of magnesium bromide. The composition may be used to treat ocular irritation caused by allergens.

Example 3

A 10 ml solution which is effective as an ear drops for ear irritations is prepared as follows:

| Ingredient | Weight |
|---|---|
| Magnesium Chloride | 0.30 mg |
| Magnesium Bromide | 0.05 |
| Magnesium Sulfate | 0.05 |
| Potasium Chloride | 0.3 mg |
| Potassium Sorbate Solution | 10.0 mg |
| Vitamin E | 0.01 |
| Purified Water | q.s. |

Optionally, about 0.05 mg of tetracycline may be added if there is prolonged infection.

Example 4

To the formulation of Example 1 is added 1.3 g of Noveon AA-1, an acrylic acid polymer available from B.F. Goodrich, 1 g mannitol 0.05 g of pluronic F127 surfactant and 10 N sodium hydroxide to arrive at a pH of 6.0.

The resulting gel could be used for either eye or ear irritations.

Preferably the composition has a viscosity of from about 1 to 50 cps.

What is claimed:

1. A method of treating a patient suffering from eye or ear inflammation or irritation which comprises topically administering an effective amount of an aqueous hypertonic composition consisting essentially of:
   A) about 0.01 to 5% by weight of salts comprising:
      1) About 45 to 60% by weight of magnesium chloride;
      2) About 29 to 40% by weight of potassium chloride, and 0% by weight of sodium chloride;
      4) about 0.5 to 4% by weight of magnesium bromide, and
   B) the remainder being water, whereby the irritation or inflammation is reduced.

2. The method of claim 1 wherein said aqueous composition is buffered at pH4.0 to 8.0.

3. The method of claim 1 which comprises including in said composition osmolarity adjusting agents.

4. The method of claim 1 which comprises wherein the osmolarity of the composition is between about 140 and 280 mOsm/l.

5. The method of claim 1 wherein said composition is a gel.

6. A method for treating eye irritations which comprises administering the composition of claim 1 by eye drops to the eye having irritations.

7. A hypertonic gel composition for treating inflammation and irritation of the eye or ear which comprises:
   A) about 0.01 to 5% by weight of salts comprising:
      1) about 45 to 60% by weight of magnesium chloride;
      2) about 20 to 40% by weight of potassium chloride;
      3) 0% by weight of sodium chloride,
      4) about 0.5 to 4% by weight of magnesium bromide, and
   B) a gelling agent,
   C) a pH buffer, and
   D) the remainder being water.

* * * * *